United States Patent [19]
Yun

[11] Patent Number: 4,986,318
[45] Date of Patent: Jan. 22, 1991

[54] FILLING VALVE FOR COUNTERPRESSURE FILLING OF CANS

[75] Inventor: Chung J. Yun, Baltimore, Md.

[73] Assignee: Crown Cork & Seal Company, Inc., Philadelphia, Pa.

[21] Appl. No.: 434,565

[22] Filed: Nov. 8, 1989

Related U.S. Application Data

[63] Continuation-in-part of Ser. No. 325,289, Nov. 27, 1981, Pat. No. 4,442,873, and a continuation of Ser. No. 125,232, Jan. 25, 1988, abandoned, which is a continuation of Ser. No. 807,440, Dec. 10, 1985, Pat. No. 4,750,533, which is a continuation-in-part of Ser. No. 574,184, Jan. 26, 1984, abandoned, and Ser. No. 796,892, Nov. 12, 1985, abandoned, which is a continuation-in-part of Ser. No. 574,184.

[51] Int. Cl.[5] .............................................. B67C 3/06
[52] U.S. Cl. ..................................... 141/39; 141/40; 141/46; 141/301; 141/6; 141/147; 141/312; 277/34; 277/152; 277/142
[58] Field of Search .......................... 277/34, 142, 152; 141/39, 40, 46, 62, 287, 301–306, 368, 369–372, 147–150, 275–278, 312, 6

[56] References Cited

U.S. PATENT DOCUMENTS

| | | | |
|---|---|---|---|
| 2,202,033 | 5/1940 | Stewart et al. | 141/148 X |
| 2,239,385 | 4/1941 | Harder | 141/148 |
| 2,663,479 | 12/1953 | Detrez . | |
| 2,770,263 | 11/1956 | Breeback | 141/6 |
| 3,090,408 | 5/1963 | Naecker | 141/57 |
| 3,478,785 | 11/1969 | Mallrich et al. | 141/39 |
| 3,516,455 | 6/1970 | Carter | 141/150 |
| 3,519,035 | 7/1970 | Remane | 141/287 X |
| 3,580,988 | 5/1971 | Orlowski et al. | 16/2 |
| 3,637,222 | 1/1972 | Wilkinson | 277/34 |
| 3,683,976 | 8/1972 | Remane | 141/287 X |
| 3,807,463 | 4/1974 | Rademacher et al. | 141/104 X |
| 3,830,265 | 8/1974 | Matejek | 141/6 |
| 3,834,428 | 10/1974 | Rademacher | 141/39 |
| 3,854,791 | 11/1974 | Friendship | 141/6 |
| 3,908,717 | 9/1975 | Rademacher et al. | 141/52 |
| 4,089,353 | 5/1978 | Antonelli | 141/302 |
| 4,124,043 | 11/1978 | Noguchi | 141/6 |
| 4,349,055 | 9/1982 | DiChiara | 141/39 |
| 4,442,873 | 4/1984 | Yun | 141/39 |
| 4,534,569 | 8/1985 | Ishitani et al. | 277/34 X |
| 4,688,608 | 8/1987 | Puskarz et al. | 141/39 |
| 4,750,533 | 6/1988 | Yun | 141/46 |

FOREIGN PATENT DOCUMENTS

| | | |
|---|---|---|
| 18495 | of 1904 | Austria . |
| 620420 | 11/1962 | Belgium . |
| 080774 | 6/1983 | European Pat. Off. . |
| 3319040 | 11/1984 | Fed. Rep. of Germany ........ 277/34 |
| 1016065 | 10/1952 | France . |
| 777929 | 7/1957 | United Kingdom . |
| 983326 | 2/1965 | United Kingdom . |

OTHER PUBLICATIONS

"Uni-Blend—Soft Drink Can Filling Equipment", Crown Cork & Seal Company, Inc. (no date).

Primary Examiner—Ernest G. Cusick
Attorney, Agent, or Firm—Woodcock Washburn Kurtz Mackiewicz & Norris

[57] ABSTRACT

Counterpressure valves for filling cans with liquids under pressure such as carbonated beverages are disclosed. In a preferred embodiment, the present invention provides a filing valve in which the seal between the valve and a can is created by an O-ring seal disposed about a valve member. Preferably, two concentric, axially-spaced O-rings are used; a first o-ring serves as a guide, while the second, slightly larger O-ring creates a seal. Since the sealing O-ring may be moved axially along the can to permit the head space volume to expand, the need for a snift valve or similar relief valve is eliminated. Sealing valves utilizing radially expandable gaskets are also disclosed. In these embodiments, the gasket expand radially under counterpressure to form a seal with the inner surface of the can.

19 Claims, 6 Drawing Sheets

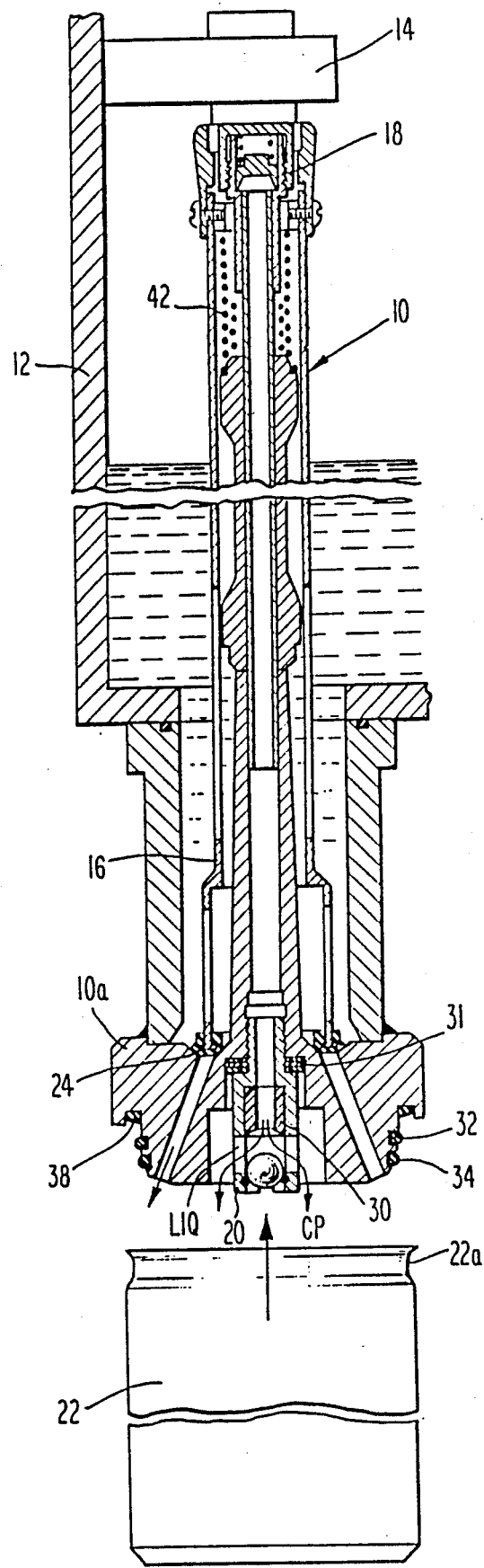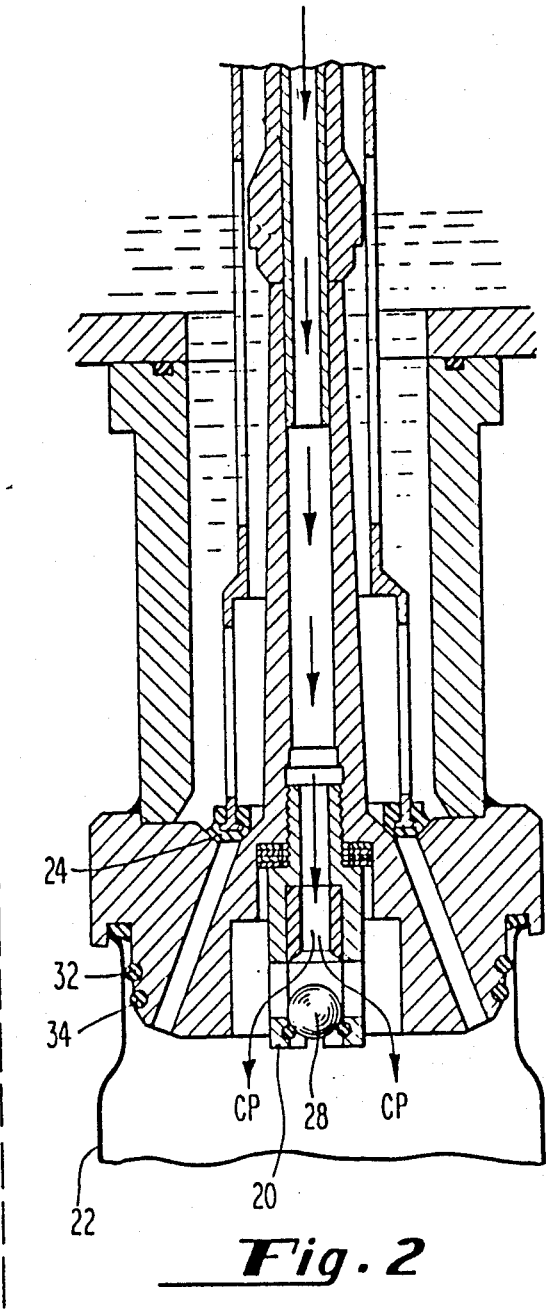
Fig. 1
Fig. 2

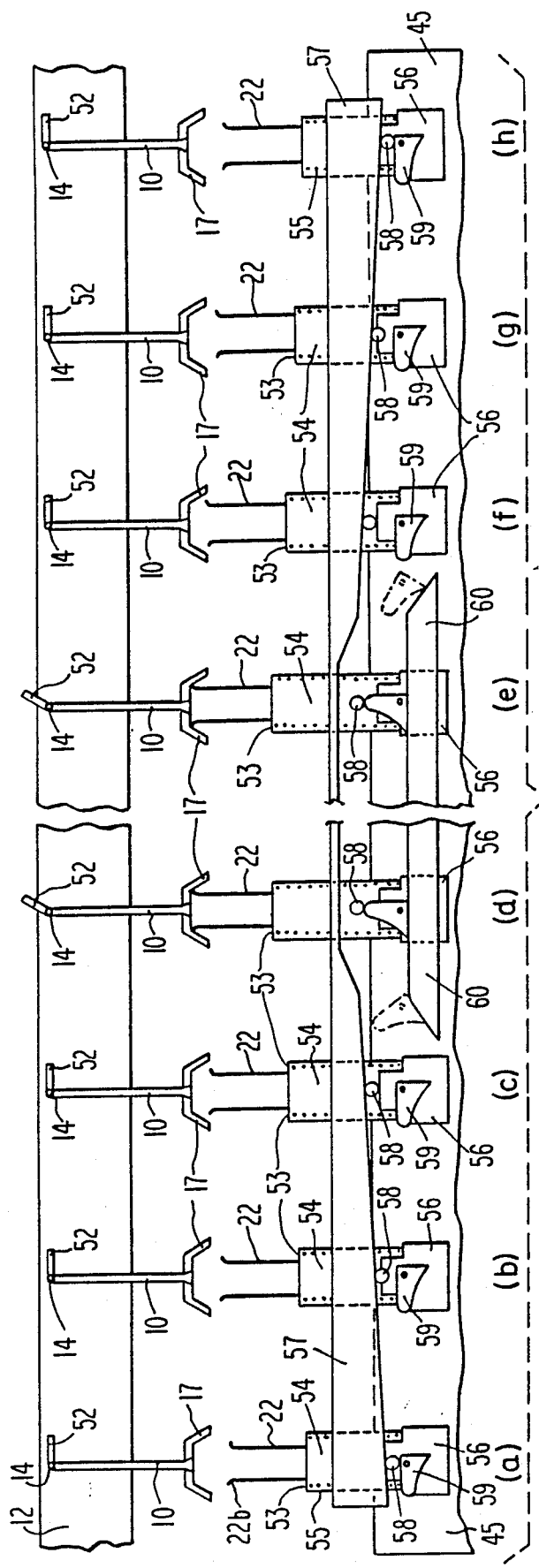
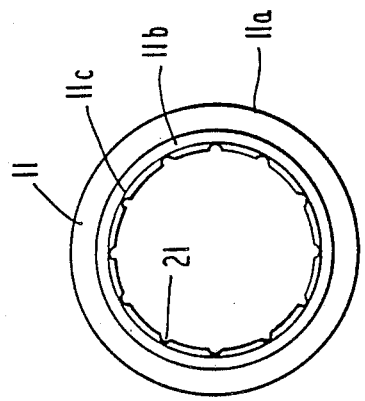
Fig.10b
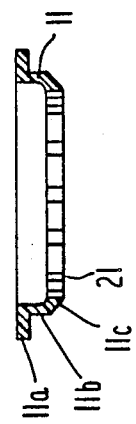
Fig.10a
Fig.12

FILLING VALVE FOR COUNTERPRESSURE FILLING OF CANS

CROSS-REFERENCE

This is ultimately a continuation-in-part of my previous U.S. Pat. No. 4,442,873 issued on Apr. 17, 1984 and assigned to the same assignee as the present invention. This is a continuation of U.S. patent application Ser. No. 125,232 filed on Jan. 25, 1988, now abandoned, which was a continuation of U.S. patent application Ser. No. 807,440, filed on Dec. 10, 1985, now U.S. Pat. No. 4,750,533, which was a continuation-in-part of both U.S. patent application Ser. No. 574,184 filed on Jan. 26, 1984, now abandoned and U.S. patent application Ser. No. 796,892, filed on Nov. 12, 1985, now abandoned, which was a continuation-in-part thereof. The former, U.S. patent application Ser. No. 574,184, was filed during the pendency of U.S. patent application Ser. No. 325,289, filed on Nov. 27, 1981 which issued as above-referenced U.S. Pat. No. 4,442,873.

FIELD OF THE INVENTION

This invention relates to improved valves for use in connection with filling of cans with carbonated beverages or the like. More particularly, the invention relates to a filling valve for use in filling of cans with carbonated beverages in which the seal between the valve and the can, which is essential for filling, is made around the inner periphery of the open end of the can rather than directly on its end, so that endloading of the can and the tendency towards consequent destruction of the can is minimized.

BACKGROUND OF THE INVENTION

Continued economic pressure in the marketplace for cans for the containment of carbonated beverages and the like has led to lighter and lighter weight construction of beverage cans. In particular, the side walls of the cans now being manufactured are thinner than ever and are consequently less durable. Difficulty is particularly encountered in counterpressure filling of cans, according to which the can is first filled with pressurized gas, and then with the carbonated liquid, so that the carbonation of the liquid does not escape upon filling. This requires that the can be sealed to the counterpressure filling valve. This is typically done by simply pressing the open end of the can into engagement with a circular resilient sealing member. However, the endloading required to effect a good seal of the counterpressure gas, which is usually at about 40 psi, is substantial, on the order of a hundred pounds. Accordingly, some percentage of the cans is ordinarily crushed. With the trend towards lighter and lighter can construction, this percentage can be expected to increase.

Most modern thin walled cans are flanged at the open end. The flange is usually formed by a lip which extends perpendicularly outward from the can. The substantial endloading caused by prior art counterpressure filling valves often caused damage and deformation of the flange since the force of endloading causes an axial deflecting moment on the flange at the perpendicular bend between the cylinder of the can and the lip. It should be noted that the flanged opening of the can is conversely relatively strong in the radial direction since the lip of the flange is approximately ten times thicker in the radial direction than in the axial direction.

Prior art attempts to obviate these problems have been unduly complex. For example, U.S. Pat. No. 3,519,035—Remane reveals a dosing device intended to be used with low temperature liquids such as liquified butane or propane. This reference discloses a filling valve which is actuated by an upward force exerted by the open end of the can or container upon the lower portion of the valve. This upward pressure is of necessity greater than the pressure required to simply support the fully fluid filled can. That is, it is necessary to maintain an upward pressure on the open end of the can in excess of the pressure required merely to hold the can in proper position during filling. Avoidance of this excessive pressure or loading is one object of the present invention. The Remane reference also discloses a sealing device comprising a tube which is inflated by an external source of pressurized gas. Expansion of the inflatable tube of Remane effects a seal on the inner diameter of the container rather than on the flanged opened end of the container. The prior art, as disclosed by Remane, thus utilized a complex two gas system that did not eliminate excessive endloading or take advantage of the relatively strong flanged open end of the container. A need, therefore, exists in the art for a relatively simple counterpressure filling valve which will provide a good seal against the escape of the counterpressure gas and the carbonated liquid, eliminate significant endloading of the can, and utilize the relatively strong flanged end of the can to make the seal.

As is well understood in the art, after filling of a can with a carbonated liquid, the head space at the top of the can, i.e. that portion of the can which is not filled with liquid, is filled with compressed gas. This must be vented to atmosphere in a so-called "snift" operation prior to removal of the can from the valve if excessive foaming and loss of product is to be avoided. In the valve shown in U.S. Pat. No. 4,442,873 this problem is solved by relative movement of the can with respect to the valve prior to cessation of the seal therebetween, such that the head space is increased sufficiently that no snift valve or the like is required. It is an object of the present invention to preserve this feature of the invention shown in the co-pending application, while forming the seal between the valve and the can without excess endloading, again so that the number of cans destroyed in the canning operation is reduced.

OBJECTS OF THE INVENTION

Accordingly, it is an object of the invention to provide an improved apparatus for the filling of cans with carbonated beverages in which the frequency of damage or destruction of the cans is reduced.

It is a further object of the invention to provide an improved valve for the filling of cans with carbonated liquids in which a seal is effected between the valve and the inner wall of the can at its open end whereby endloading of the can to form a seal is avoided.

It is a further object of the invention to provide an apparatus for the filling of cans with carbonated liquid in which no snift valve for venting the head space of the can after filling is required.

It is a still further object of this invention to provide an improved seal for the filling of cans with carbonated liquid in which a seal is effected between the filling device and the can whereby the potential for damage to the flanged portion of the can is reduced.

SUMMARY OF THE INVENTION

The above mentioned needs of the art and objects of the invention are satisfied by a first embodiment of the present invention which provides a filling valve in which the seal between the valve and a can to be filled with carbonated beverage is effected between the inner surface of the can at its open end and an O-ring disposed about a valve member. Two concentric, axially spaced O-rings are used; one is slightly smaller than the diameter of the inside of the can, and provides a guide for the can, which is sealed to a slightly larger O-ring spaced axially along the valve body away from the smaller O-ring, so that upon bringing the can into engagement with the valve, the can end first passes over the guide O-ring and then forms a seal with the sealing O-ring. Cans are now made according to industry standard with a cylindrical neck portion of invariant diameter at their open ends. This first embodiment utilizes this fact by providing a valve with a sealing O-ring which interacts with the inner surface of the neck portion. The fact that the cylindrical neck portion extends some distance axially along the can allows the can to be moved that distance with respect to the valve after filling without breaking the seal. Accordingly, the head space volume expands after filling, which eliminates the need for a snift valve or the like.

A second embodiment of the present invention is a filling valve in which the seal between the valve and a can to be filled with carbonated liquid is effected between a radially expandable gasket, disposed about a valve member, and the inner surface of the flanged portion of the can. A first portion of the flexible gasket is in sealable engagement with the valve member. A second portion of the gasket has an inner surface spaced from a surface of the valve member and an outer surface in contact with the inner surface of the flanged portion of the can. When counterpressure gas enters the can, the space between the valve member and gasket is pressurized, and the gasket expands into sealing engagement with the inner surface of the flanged portion of the can. This embodiment of the invention exerts sealing pressure substantially in the radial direction with respect to the flanged portion of the can.

BRIEF DESCRIPTION OF DRAWINGS

FIG. 1 shows a cross-sectional view of a valve made according to a first embodiment of this invention.

FIGS. 2 through 4 are cross-sectional views of a valve made according to the first embodiment of this invention showing the end of the valve at varying stages in the can filling process.

FIG. 10a is a radial cross-sectional view of the sealing gasket made according to the second embodiment of this invention.

FIG. 10b is a plan view from above of the sealing gasket made according to the second embodiment of this invention.

FIGS. 12a–12h are cross sectional views of a filling apparatus made according to the third embodiment of this invention showing varying stages in the can filling process.

DESCRIPTION OF THE PREFERRED EMBODIMENT

Description of Common Features

While two embodiments of this invention are disclosed, several features of this invention are common to both. Items which are common to both embodiments have been marked by the same symbol, and are described below.

Figure 5:
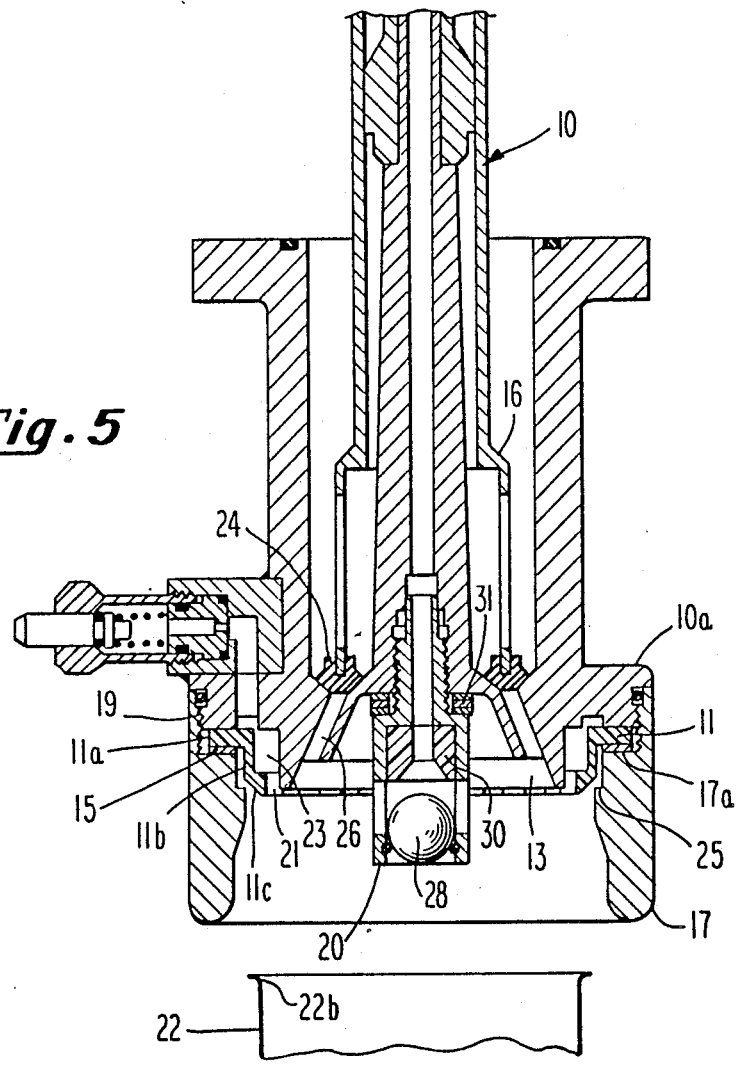
FIG. 5 is a cross-sectional view of a valve made according to a second embodiment of this invention.
Figure 8:
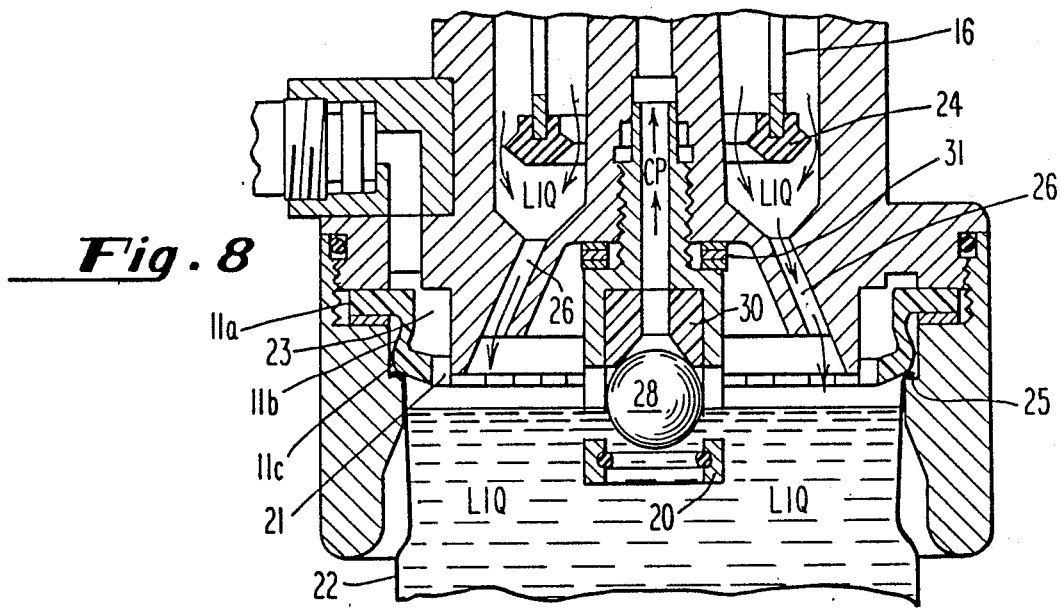

Referring to FIGS. 1, 5, and 8, both disclosed embodiments of this invention use a valve 10 for fluid communication between can 22 and the fluid to be canned. The valve 10 is shown within reservoir 12 which, as is conventional in the art, is filled with the liquid to be canned; above the liquid is a gas at elevated pressure, typically nitrogen or carbon dioxide at 40–45 psi. The valve 10 is operated by a conventional cam member 4. The construction and operation of the cam and of the valve are generally as described in commonly assigned U.S. Pat. No. 4,089,353 to Antonelli. The valve 10 comprises two relatively movable valve members 16 and 18 Upon actuation of the valve member 18 by the cam 14, counterpressure gas is permitted to flow down through the center of the valve, out around a check valve ball 20 and into the can 22, as indicated by the arrows marked CP. Upon actuation of the second valve member 16, by the action of compression spring 42, the seal formed between a resilient valve member 24 and the body 10a of the valve 10 is broken, allowing liquid to flow downwardly around the valve member 24 and into the can 22 as indicated by arrows marked LIQ. At the same time counterpressure gas flows back upwardly through the center of the valve. When the liquid level raises the relatively buoyant ball 28 of the ball check valve 20, a seal is formed between the ball 28 and a resilient sealing member 30, preventing the expulsion of further counterpressure gas and influx of liquid into the can. As shown, the ball check valve housing 20 is threadedly connected to the body of the valve 10. The number of spacers 31 interposed therebetween may be varied to adjust the relative volume of the head space remaining in the can after the ball check valve has caused filling to cease.

First Embodiment

Figure 3:
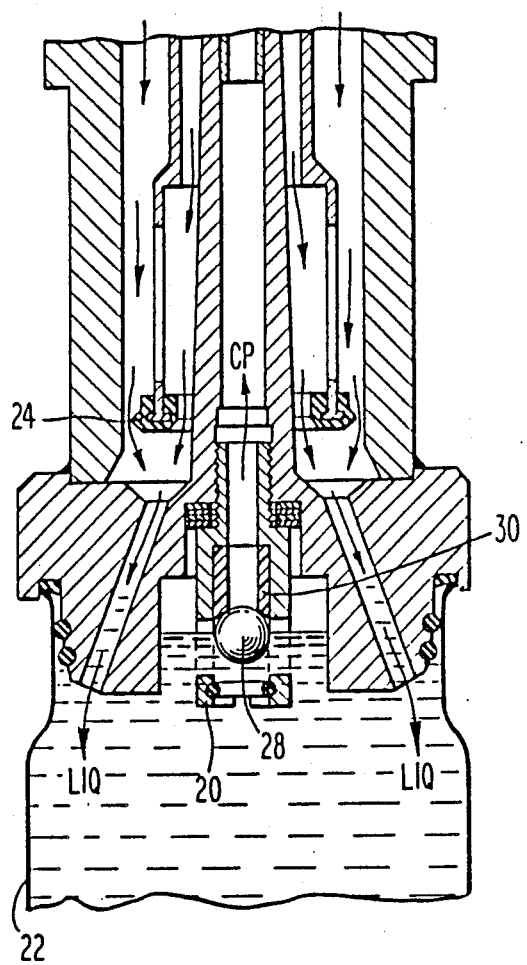
Figure 4:
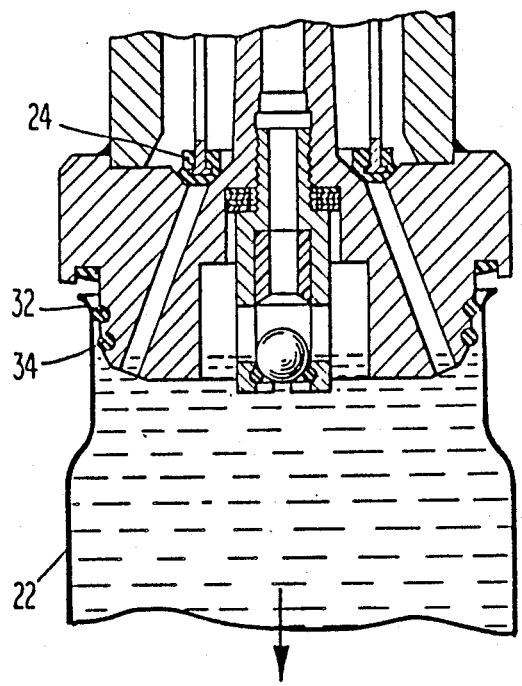

It will be observed from FIG. 1 and as shown in FIGS. 2 through 4 that two O-ring seals 32 and 34 are provided with a valve made according to the first embodiment of this invention. They are of slightly different diameter; the O-ring 34 disposed more toward the end of the valve is smaller, and acts as a guide to center the can on the valve as the can is raised into engagement therewith by conventional lifters (not shown) or lifters as described later in the specification. The other O-ring 32 is used to seal the valve to the can by fitting tightly into the generally cylindrical neck portion 22a of the can 22. The industry standards defining the shape of the can provide that the cylindrical neck portion 22a is at least about 0.180 inches long in most industry standard cans. This cylindrical surface allows relative motion of the valve with respect to the can without breaking the seal formed therewith by the larger O-ring 32, which allows expansion of the head space after filling so as to provide equalization of the counterpressure gas to atmospheric pressure without a snift valve or the like. As mentioned, the headspace volume after filling of the can may be varied by adjusting the number of spacers 31 interposed between the ball check valve housing 20 and the valve 10. The headspace volume is selected so that when the can is allowed to drop away from the valve 10 after being filled, its head space volume increases proportionally so that the pressure of the gas in the head space is reduced to atmospheric or thereabouts. Since the counterpressure gas is typically at 45 psi, this requires a 3:1 increase in the volume of the head space; clearly if canning is carried out at high altitudes this volume will typically be increased to compensate for the lower atmospheric pressure at these altitudes.

As mentioned, the two O-rings 32 and 34 are slightly different in diameter The O-ring 34 located towards the nether end of the valve according to the invention is slightly smaller, typically two millimeters less in diameter than the larger O-ring 32. In this way, the smaller O-ring 34 provides a guide function, insuring that the can flange is concentric with the valve upon raising of the can into contact with the valve for filling The smaller O-ring 34 also prevents contact of the inner surface of the can and the metal of the valve body, so that the inner sealing surface is not scratched or damaged in filling. In the preferred embodiment the O-rings are standard parts and fit into grooves in the valve body sized as specified by the O-ring manufacturers, to insure a good seal. The precise O-ring size chosen will vary in accordance with the cans to he filled.

In FIG. 1 there is shown an additional resilient member 38, which contacts the flange of the can 22. However, it should be appreciated that according to the present invention this member 38 is not required to provide an adequate gas-tight seal between the valve 10 and the can 22, that function being provided by O-ring 32, but instead is merely provided as a bumper or travel limiter, insuring that the O-ring 32 remains in contact with the cylindrical neck portion 22a of the can 22.

FIGS. 2 through 4 show three successive-stages in the filling of a can with the valve according to the first embodiment of the invention. FIG. 2 shows the can having been lifted into engagement with valve 10; ball check valve 28 is resting downwardly and the valve member 24 is closed. As the can 22 moves upwardly it first encounters the smaller O-ring 34 which helps guide it over the larger sealing O-ring 32 until it reaches the position shown in FIG. 2. Subsequently, when the upper valve 18 is opened by the cam 14 (FIG. 1), counterpressure gas flows down the center of the tube and out around the ball check valve 28 into the can as shown by the arrows marked CP in FIG. 2. Subsequently, the cam allows the second valve member 24 to be lifted by spring 42 (FIG. 1) as shown in FIG. 3, and liquid flows into the can, through a number of ports in the valve 10a as shown by the arrows marked LIQ. The counterpressure gas flows upwardly out of the can as indicated by the arrow marked CP. Eventually the liquid level reaches the point shown in FIG. 3, when the buoyant ball 28 of the check valve is moved upwardly against the sealing member 30, ending the flow of counterpressurized gas upwardly up the center of the valve, which in turn prevents further liquid from entering the can. It will be understood by those skilled in the art that as the gas and liquid are in the same tank, as shown in FIG. 1, their pressures are equal and hence liquid flow stops when gas no longer can escape from the can. It will also be appreciated by those skilled in the art that this method of shutting off liquid flow is positive and accurate, as discussed in the Antonelli U.S. Pat. No. 4,089,353 mentioned above, unlike certain prior art methods of ending liquid flow in canning operations, e.g., using the surface tension of the liquid in conjunction with a capillary screen placed in the liquid flow path, or the like.

After filling, lifters, as described latter in the specification for example, allow the can to drop away from the valve. FIG. 4 shows the can moving away from the valve while the seal between the neck of the can and O-ring is maintained. At this point the upper valve 18 has been shut by the cam 14 so that the volume of the head space in the can is increased as the can moves down away from the valve, as shown in FIG. 4. This allows the compressed gas confined above the liquid in the valve 10 to expand until its pressure is substantially equal to atmospheric pressure, preventing excessive foaming of the liquid when the can moves fully out of engagement with the valve, preparatory to being capped in the conventional fashion. As shown in FIG. 4, the sealing member 24 has also been reseated on the valve body (by the cam 14 of FIG. 1) so as to prevent escape of the liquid upon the can being removed from the valve.

It will be appreciated by those skilled in the art that this embodiment describes a novel valve for counterpressure filling of containers with carbonated liquids and the like, in which the seal between the valve and the can, essential for proper counterpressure filling of cans, is made between the valve and a generally cylindrical inner surface of the can, thus avoiding high endloads associated with end-effected seals, and minimizing can crushing and flange damage, thus tending to improve reliability of the canning operation.

Second Embodiment

While the valve set forth and described in connection with FIGS. 1-4 has met with some success in eliminating detrimental can endloading, it has been found that stripping or removing filled cans from the valve has, at times, been difficult. Accordingly, an improved sealing means has been devised which not only solves the aforementioned endloading problem but which also solves the stripping problem as well This improved valve is described in connection with FIGS. 5-10b.

The improved sealing means 11 of the second embodiment replaces the O-rings 32 and 34 of FIG. 1 and is shown in detail in FIGS. 10a and 10b. As shown in FIG. 10b, the sealing means 11 is a solid ring-shape gasket. The sealing means 11 is an integral body having three distinct portions 11a, 11b and 11c which will be described below. In accordance with a preferred aspect of this embodiment of the present invention, the sealing means 11 has a plurality of radially and axially extending notches 21 extending radially outward from the inner diameter of the ring-shaped gasket. The function of these notches will be made clear below.

Referring now to FIG. 5, the relationship of the sealing means 11 and the valve 10 will be seen.. The sealing means 11 is situated about the cylindrical projection 13 extending from valve body 10a.

The sealing means 11 is comprised of a first cylindrical ring 11a, integral with a second cylindrical ring 11b, and a third cylindrical ring 11c. The sealing means 11 is held in sealing engagement with the lower surface of the valve body 10a by support washer 15. Support washer 15 is in turn held in place by a first inner lip 17a of the bell housing 17. Bell housing 17 is threadedly coupled to valve body 10a as shown by symbol 19.

First ring 11a of seal means 11 forms a seal between the lower surface of valve body 10a and bell housing 17. The force necessary to seal the upper surface of ring 11a with the lower surface of valve body 10a is supplied by the compression force exerted by support washer 15 when bell housing 17 is coupled to the valve body. The inner diameter of ring 11a is greater than the outer diameter of cylindrical projection 13. Depending from cylindrical ring 11a is second cylindrical ring 11b. The inner diameter of ring 11b is equal to the inner diameter of ring 11a, and the outer diameter of ring 11b is less than the inner diameter of that portion of bell housing 17 adjacent to ring 11b. Ring 11c depends from ring 11b and is in contact with the outer surface of cylindrical projection 13. The outer surface of ring 11c depends at a substantially 45° angle from ring 11b so as to contact the curved portion of flanged end 22b of can 22 in a substantially tangential manner when the can is brought into contact with sealing means 11.

Figure 6:
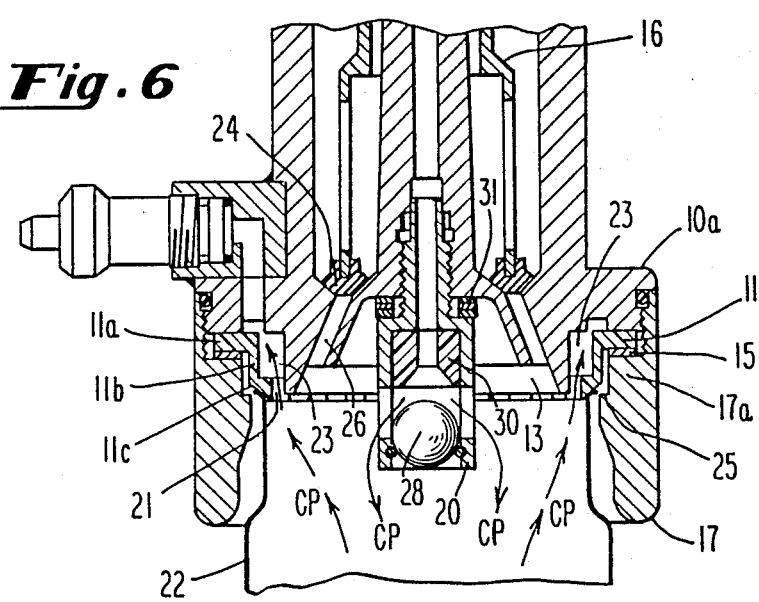
FIGS. 6–9 are cross-sectional views of a valve made according to the second embodiment of this invention showing the end of the valve at varying stages in the can filling process.

In accordance with an important aspect of the present invention, the sealing means 11 comprises a self-inflating solid expandable gasket which expands radially into sealing engagement with flange 22b of can 22 by virtue of counterpressure gas which flows from reservoir 12 into can 22. The operation of the expandable gasket is shown in FIGS. 6–9 FIGS. 6 through 9 show four consecutive stages in the filling of a can with a valve made according to this embodiment of the invention and disclose the manner in which the expandable gasket affects sealing engagement with the flanged portion 22b of can 22. Referring to FIG. 6, can 22 is shown in a position in which it has just been lifted into engagement with valve 10 by a conventional lifter, or the lifter described later in the specification, wherein the lifting force of said lifter does not cause excessive endloading on the can 22. In the stage shown in FIG. 6, the interior of can 22 is sealed from the counterpressure gas and the carbonated liquid by valve members 18 and 16 respectively. That is, the pressure inside can 22 is equal to the pressure outside can 22.

One can 22 is lifted into engagement with gasket 11, upper valve member 18 is opened by cam 14 (FIG. 1). With valve member 18 in the open position counterpressure gas flows through valve 10, around ball check valve 28, and into can 22. See the arrows marked by CP in FIG. 6. As the counterpressure gas fills can 22, it will also pass through semicircle notches 21 in gasket 11 and into chamber 23, which is formed by the inner surface of cylindrical projection 13, the inner surface of gasket 11 and the lower surface of valve body 10a. It should be noted that when the counterpressure gas first enters can 22 there is insufficient force exerted on can 22 to form a complete seal between the opening of can 22 and gasket 11. However, the contact between the flanged end 22b of can 22 and the angular portion of ring 11c of gasket 11 is sufficient to cause the preferential flow of counterpressure gas into semicircular notches 21 rather than between can opening 22b and ring 11c. This initial preferential flow of counterpressure gas into chamber 23 causes an increase in pressure in chamber 23 which in turns causes radial expansion of rings 11b and 11c of gasket 11. This expansion of gasket 11 causes a uniform radial sealing pressure between the outer surface of ring 11c and the inner surface of flanged opening 22b. This improved sealing contact between gasket 11 and can 22 thus maintains the preferential flow of counterpressure gas through notch 21 and into chamber 23 as the can fills with counterpressure gas.

Figure 7:
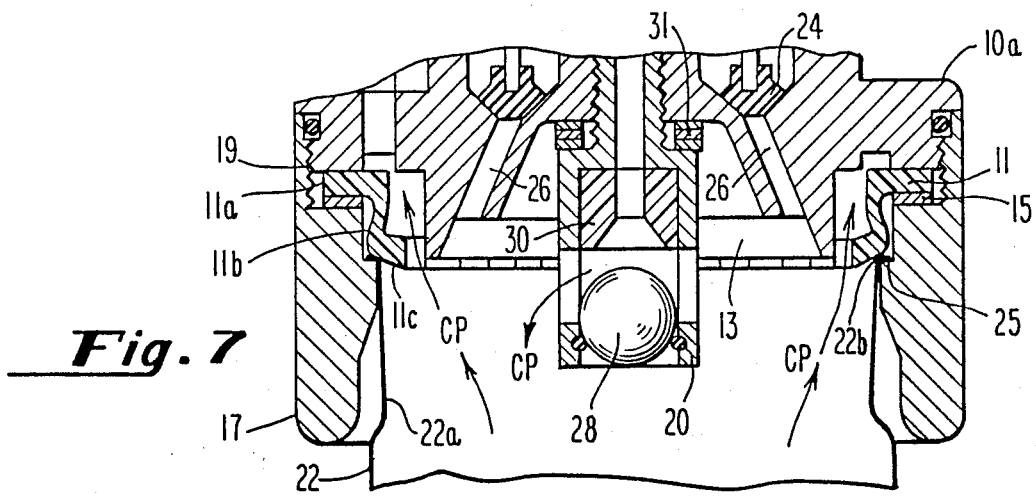

FIG. 7 shows that stage of filling in which can 22 has been filled with the counterpressure gas and the pressure within can 22 has equilibrated to the pressure of the counterpressure gas. Due to the differential in pressure between the atmosphere within bell housing 17 and the pressure within chamber 23, gasket 11 expands in a generally radially outward direction. This expansion causes the outer surface of gasket 11 to exert a sealing pressure on the inner surface of flange 22b. This pressure results in a conformation between the outer surface of ring 11c and the inner surface of flanged end 22b, which in turn results in a seal between the can and valve 10. In addition, the uniform radial pressure exerted by the expansion of gasket 11 causes a slight increase in the diameter of the opening of can 22. The interior of bell housing 17 contains a support lip 25 which serves to stabilize and support the flanged end 22b of can 22 if the opening of the can responds to the pressure exerted by expandable gasket 11.

Referring to FIG. 8, once the interior of the can has equilibrated with the counterpressure gas, cam 14 allows the second valve member 24 to be lifted by spring 42 (FIG. 1), and liquid flows into the can through liquid ports 26 in valve body 10a. The counterpressure gas within the can is displaced by the entering liquid and flows upward out of the can and back into the reservoir as indicated by the arrow marked CP. Eventually the liquid level reaches the point as shown in FIG. 8, when the buoyant ball 28 of the check valve is moved upwardly against the sealing member 30, ending the flow of counterpressurized gas upwardly through the center of the valve, which in turn prevents further liquid from entering the can.

Figure 9:
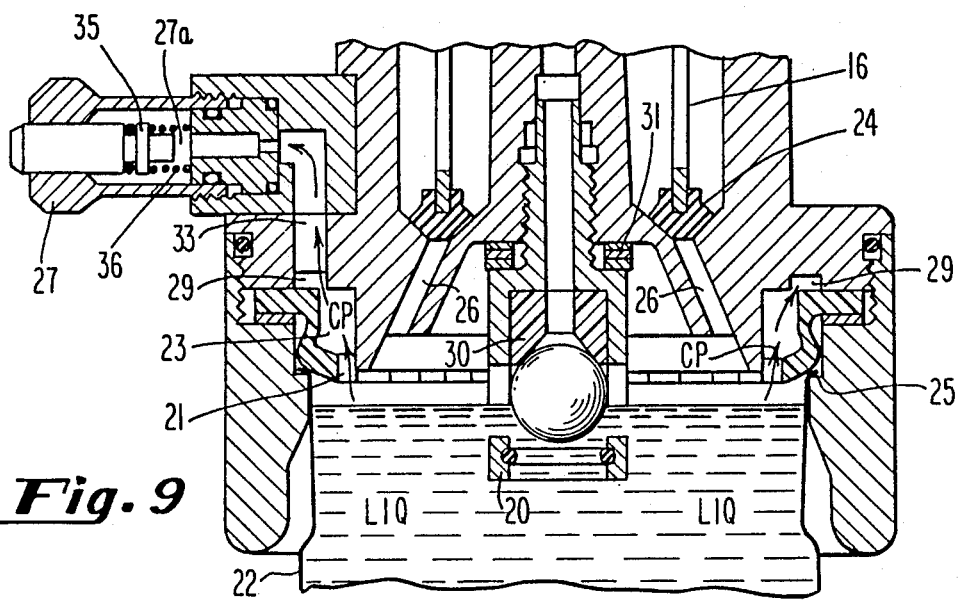

Referring to FIG. 9, the snifting and disengaging stage of the can filling process is shown. In this stage of operation, cam 14 has moved valve members 18 and 24 into sealed position thereby isolating valve body 10a from reservoir 12 (FIG. 1). Escape of the residual counterpressure gas contained within the head space of the can is achieved through snift valve 27. Chamber 27a of snift valve 27 is in fluid communication with the head space of can 22 through the passage provided by notches 21 in gasket 11, annular slot 29 in valve body 10a, the port 33 in valve body 10a. The outlet portion of snift valve 27 is normally sealed from chamber 27a by snift valve O-ring 35. When snift valve 27 is actuated by conventional means against the urgence of spring 36, O-ring 35 is disengaged from its sealing position with respect to snift valve 27 and counterpressure flows from the head space in can 22 through snift valve 27 to a low pressure reservoir (not shown). As the counterpressure gas passes through snift valve 27 the pressure differential between chamber 23 and the exterior of can 22 is reduced thus disengaging the seal between ring 11c and flange portion 22b of can 22. As a result the snifting operation also serves to disengage the seal between valve 10 and can 22. When sufficient counterpressure gas flows through valve 27 into the low pressure reservoir, snift valve 27 is moved with the urgence of spring 36 back into the sealed position. At this point, conventional lifters or the lifters shown latter in the specification allow the can to drop away from the valve. The valve is then ready for a new cycle of filling.

Gasket 11 is generally made of a flexible elastic material. While this is generally true of the entire gasket, it is particularly true for rings 11b and 11c. These two portions of the gasket must be sufficiently flexible to respond to the appropriate pressure differential. The elasticity required to achieve this deformation is a function of many parameters; such as, diameter of the gasket, length of ring 11b, exact pressure differential, and others. Whatever elasticity is used to accommodate these parameters is within the scope of this invention.

The first and second embodiment of this invention find particular utility with the filling machine disclosed in FIGS. 11 and 12a-12h. That filling machine comprises a carousel type filling apparatus in which a plurality of cans are filled with carbonated liquid as the carousel revolves around a central point. In this arrangement the cans are lifted by a lift cylinder into a filling position with respect to the apparatus without producing excessive endloading on the open end of the can. The cans are placed, by conventional means, on the lift cylinder which is aligned with and spaced from the valve used for filling the cans. In this disengaged position, the space between the top of the lift cylinder and the bottom of the filling valve is greater than the longitudinal length of the can. As the carrousel rotates the lift cylinder moves the can to be filled into an engaged position with the filling valve. The can fills as the carrousel rotates. After the cans are fully fluid filled, the lift cylinder retracts and allows the can to disengage from the filling valve. Upon disengagement, the can, full of carbonated liquid, is removed from the cylinder by conventional means and an empty can to be filled takes its place on the lift cylinder.

Figure 11:
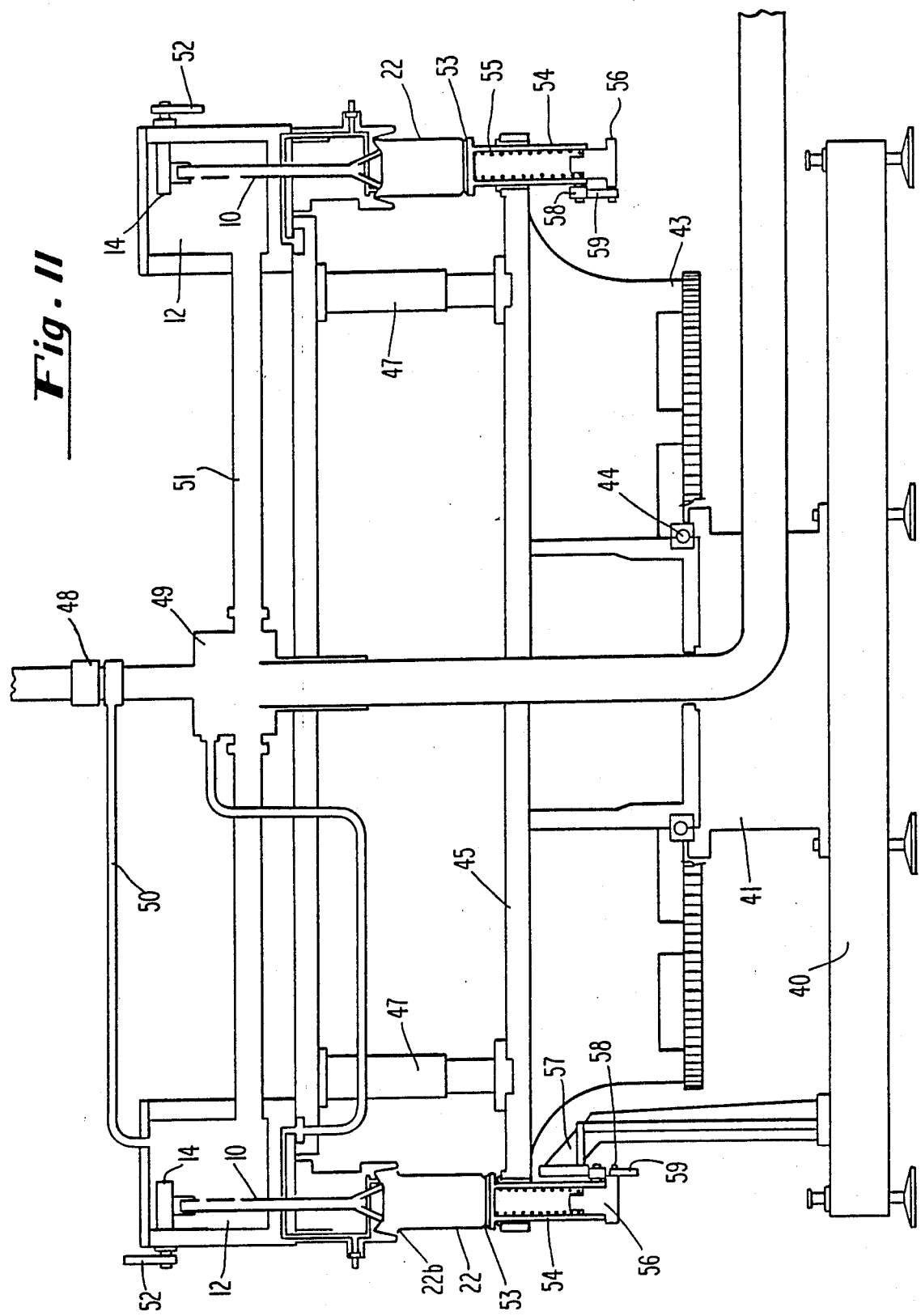
FIG. 11 is a schematic view of a filling apparatus made for use with the first and second embodiment of this invention showing the lifting cylinders made according to this invention.

An important aspect of the can filling apparatus of FIGS. 11 and 12 is that the lift cylinders impose substantially no load upon the cans as they are being filled. Instead, the lift cylinders simply raise the cans into filling position and restrain them from movement from that position against the force of the fluid with which the can is to be filled This feature, in combination with the improved sealing techniques of the embodiments of FIGS. 1-4 and FIGS. 5-10b is particularly useful in avoiding endloading while at the same time permitting an adequate fluid seal between the valve and the can.

Referring to FIG. 11, a schematic view of the apparatus which accomplishes this objective is shown. The entire apparatus is supported by base 40 which is mounted to or rests on a conventional footing. Mounted on the base is a drive motor 41. Main drive gear assembly 43 is in rotational engagement with drive motor 41 and is supported by base 40 through main bearings 44. Cylindrical support casting 45 is mounted to the main drive gear assembly 43. Reservoir 12 contains the carbonated liquid and counterpressure gas used in filling the cans and is mounted to cylindrical support casting 45 by vertical support member 47. Reservoir 12 is generally cylindrical in shape and being ultimately supported by the main drive gear assembly 43 is rotatable thereby. Reservoir 12 is centrally disposed about and in fluid communication with counterpressure gas feed hub 48 and carbonated liquid feed hub 49. These feed hubs are in rotatable and sealable engagement with a counterpressure gas feed line 50 and a carbonated liquid feed line 51 respectively. In this way a constant supply of counterpressure gas and carbonated liquid is supplied to the reservoir 12 even as it rotates.

Depending from and extending into reservoir 12 is valve 10. The upper end of valve 10 is in fluid communication with the counterpressure gas while the lower portion of valve 10 is in fluid communication with the carbonated liquid. Valve actuating arm 52 is connected to cam 14 contained within the reservoir and in contact with valve 10. Valve actuating arm 52 is used to dispose cam 14 with respect to valve 10 in the various operating positions as disclosed in the description of the common features.

Referring to FIGS. 12a through h, a series of eight sequential views of a can being engaged and disengaged to a filling valve by the carrousel apparatus previously described is shown. FIG. 12a shows the initial stage in which can 22 has just been moved into position on platform 53 of lift cylinder 54. Lift cylinder 54 is slidably mounted to cylinder support casting 45 for movement towards and away from filling valve 10. Contained within cylinder 54 is a means for urging platform surface 53 towards filling valve 10 such that exertion of this force will not cause excessive endloading on can 22 when the can is placed between platform surface 53 in filling valve 10. Specific embodiments of urging means 55 are discussed later in the specification.

As revealed in FIG. 12a when can 22 is first placed on platform 53, lift cylinder 54 is prevented from moving towards filling valve 10 by first ramp 57 which is fixedly mounted to base 40 The lower surface of ramp 57 is in an interfering position with respect to roller pin 58 which is fixedly mounted to cylinder 54. As revealed in FIGS. 12a through d, the lower surface of ramp 57 slopes towards filling valve 10 in the direction of movement of the filling valve. As a result, can 22 is moved into engagement with filling valve 10 as the apparatus is rotated. Referring specifically to FIG. 12d, as roller pin 58 moves to the end of ramp 57, stopping cam 59 which is pivotally mounted to lift cylinder base 56 engages second ramp 60 which is fixedly mounted to base 40. Interference between stopping cam 59 and second ramp 60 moves stopping cam 59 into a position in which it prevents the downward movement of lift cylinder 54 during the filling operation. During the filling operation the lift cylinder 54 imposes substantially no load upon can 22 except as may be necessary to prevent movement of the can away from filling valve 10.

Once can 22 has been moved into the filling position disclosed in FIG. 12d, the can is sealed and filled according to the description of this invention disclosed earlier in the specification. Once this operation is complete, can 22 is disengaged from the filling apparatus as disclosed in FIGS. 12e through h. These figures reveal that disengaging can 22 from filling valve 10 is substantially the inverse of the engaging operation. That is, ramp 57 has a lower surface in this portion of the apparatus which slopes away from filling valve 10 and interferes with roller pin 58 while second ramp 60 also slopes away from filling valve 10 thus allowing disengagement of stopping cam 59 from an interfering position with respect to roller pin 58. As a result, the interference of lower surface of ramp 57 with pin 58 results in the slow disengagement of can 22 from filling valve 10. The can as shown in FIG. 12h is ready for removal from the filling apparatus.

Any urging means (e.g., a resilient means such as the coil spring shown schematically as contained within the lift cylinder 54 in FIGS. 11 and 12a-h) used for engaging can 22 with filling valve 10 without causing excessive endloading of the can is within the scope of this invention. The purpose of the urging means 55 is to move the can to be filled into engagement with the filling valve 10. In order to fulfill this purpose, the urging force must, at a minimum, exert sufficient force to overcome the weight of the empty can. A filling valve which requires substantially only this minimum urging force is the ideal valve with respect to elimination of endloading on the cans. This ideal valve is closely approximated when the first and second embodiments of this invention are used in conjunction with the filling machine disclosed in FIGS. 11 and 12 and described above. That is, since both embodiments of the present invention require substantially no endloading of the can to effect the seal between the can and the filling valve, and the stopping cam 59 prevents downward movement of the lift cylinder 54 once the can has been moved to an engaged position with respect to the filling valve, the urging force of urging means 55 need only be that minimum urging force required to overcome the weight of the empty can or at least, the force created by a fully fluid filled can.

While two specific embodiments of this invention have been disclosed, modifications are within the true spirit and scope of this invention. The appended claims are therefore intended to cover all such modifications.

I claim:

1. A valve for the counterpressure filling of cans with a pressurized fluid comprising:
    (a) a valve body;
    (b) valve member movable with respect to said valve body from a closed position to a substantially open position for dispensing the pressurized fluid to the cans;
    (c) sealing means coupled to said valve body for sealing the cans to the valve body, said sealing means comprising a flexible ring-shaped member movable from a normally unexpanded position to an expanded position, said ring-shaped member being moved by said pressurized fluid from said normally unexpanded position to said expanded position such that in said expanded position said flexible ring-shaped member exerts a radial sealing pressure on said cans.

2. A valve as recited in claim 1 wherein said sealing means is an expandable gasket.

3. The valve recited in claim 2 wherein said expandable gasket is a solid ring-shaped gasket expandable in the radial direction.

4. A valve for counterpressure filling of cans with carbonated liquid and counterpressure gas, said cans being of the type having a flanged open end, said valve comprising:
    (a) a valve body;
    (b) a first valve member movable with respect said valve body from a closed position to a substantially open position for dispensing the counterpressure gas to the cans;
    (c) a second valve member movable with respect to said valve body for dispensing the carbonated liquid to the cans; and
    (d) sealing means coupled to said valve body for sealing the cans to the valve body without excessive endloading, wherein said sealing means comprises an expandable gasket movable from a normally unexpanded position to an expanded position, said gasket being displaced by entry of the counterpressure gas into the cans such that said gasket exerts a radial sealing pressure on said cans whereby said sealing means moves into sealing engagement with the flanged open end of the cans substantially when said first valve member moves to its open position.

5. A valve as recited in claim 4 wherein said sealing means is an expandable gasket.

6. The valve recited in claim 5 wherein said expandable gasket is a solid ring-shape gasket expandable in the radial direction.

7. An apparatus for the counterpressure filling of cans with pressurized fluid comprising:
    (a) a valve body;
    (b) a valve member movable with respect to said valve body from a closed position from a closed position to a substantially open position for dispensing the pressurized fluid;
    (c) sealing means coupled to said valve body for sealing the cans to the valve body without excessive endloading, wherein said means comprises an expandable gasket movable from an unexpanded position to an expanded position, said gasket being displaced by entry of the pressurized fluid into the cans such that said sealing means moves into sealing engagement with the cans substantially when said valve member moves to its open position; and
    (d) means for moving said cans into a filling position in engagement with said sealing means without excessive endloading of the cans.

8. The apparatus of claim 7 wherein said sealing means is an expandable gasket.

9. The apparatus of claim 8 wherein said expandable gasket is a solid ring-shape gasket expandable in the radial direction.

10. The apparatus of claim 7 wherein said means for moving said cans into filling position without excessive endloading comprises:
    (a) a movable lift cylinder in axial alignment with said valve body, said lift cylinder being movable between a disengaged position and an engaged position, said cans being in said filling position whenever said lift cylinder is in said engaged positions; and
    (b) means for urging said lift cylinder towards said valve body with substantially only that force required to overcome the opposing force of a fully fluid filled can.

11. The apparatus of claim 10 wherein said means for urging exerts a force substantially no greater than that force required to overcome the opposing force of an empty can.

12. The apparatus of claim 11 further comprising a cam movable between a non-interfering position with respect to said lift cylinder and an interfering position in which said cam prevents the movement of said lift cylinder from said engaged position.

13. The apparatus of claim 10, wherein said urging means is a resilient means contained within said lift cylinder.

14. The apparatus of claim 10 further comprising:
    (a) a movable support housing to which said valve body is mounted;
    (b) means for moving said support housing;
    (c) means responsive to the movement of said support housing for moving said lift cylinder with the urgence of said urging means from said disengaged position to said engaged position.

15. The apparatus as recited in claim 14 wherein said means responsive to the movement of said housing comprises:
    (a) a pin mounted to said lift cylinder;
    (b) a ramp fixed with respect to said housing having a surface which slopes towards said valve body in the direction of movement of said housing, said ramp interfering with said pin such that said pin is biased against said sloping surface thereby moving said lift cylinder towards said valve body as said housing moves.

16. The apparatus as recited in claim 14 further comprising: a cam pivotally mounted to said housing and movable between a non-interfering position with respect to said lift cylinder and an interfering position in which said cam prevents the downward movement of said lift cylinder; and means responsive to the movement of said housing for moving the cam into said interfering position when the cans are in said filling position.

17. A sealing device for use with a filling valve for counterpressure filling of cans with pressurized fluid, wherein said filling valve is adapted for movement from a closed position to a substantially open position, said device comprising:
 (a) a flexible member moved by entry of pressurized fluid into the cans from a normally unexpanded position to an expanded position such that said flexible member exerts a radial sealing pressure on said cans substantially when the filling valve moves to its open position.

18. The sealing device of claim 17 wherein said flexible member comprises an expandable ring-shaped gasket.

19. The sealing device of claim 18 wherein said gasket has a plurality of notches on the inner surface thereof.

* * * * *